United States Patent [19]
Abdou

[11] 4,247,634
[45] Jan. 27, 1981

[54] CULTURE CUP AND METHOD FOR SAMPLING AND MICROBIAL-COUNT DETERMINATION

[75] Inventor: Mohamed Abdou, Hausen, Fed. Rep. of Germany

[73] Assignee: Biotest-Serum-Institut GmbH, Frankfurt, Fed. Rep. of Germany

[21] Appl. No.: 41,223

[22] Filed: May 21, 1979

[30] Foreign Application Priority Data

May 26, 1978 [DE] Fed. Rep. of Germany ... 7815774[U]

[51] Int. Cl.³ ............................................. C12Q 1/08
[52] U.S. Cl. ....................................... 435/40; 220/20; 229/2.5 R; 229/15; 435/32; 435/33; 435/34; 435/39; 435/296; 435/297; 435/298; 435/301
[58] Field of Search .................. 435/29, 30, 31, 32, 33, 34, 39, 40, 296, 297, 298, 299, 300, 301; 229/2.5, 15; 220/20

[56] References Cited

U.S. PATENT DOCUMENTS

| | | | |
|---|---|---|---|
| D. 223,657 | 5/1972 | Reifers et al. | 229/2.5 |
| 1,865,742 | 7/1932 | Chapman | 229/2.5 |
| 2,036,572 | 4/1936 | Frost | 229/2.5 |
| 3,055,808 | 9/1962 | Henderson | 435/301 X |
| 3,098,597 | 7/1963 | Johnson et al. | 229/2.5 |
| 3,521,788 | 7/1970 | Kandel et al. | 229/2.5 |
| 3,816,264 | 6/1974 | Winter et al. | 435/298 |

Primary Examiner—Robert J. Warden
Attorney, Agent, or Firm—Sprung, Felfe, Horn, Lynch & Kramer

[57] ABSTRACT

A culture cup for sampling and microbial-count determination, comprising a body and a tightly closing removable lid, the bottom of the body being provided with depressions for accomodation of at least one culture medium. The lid on its underside may be provided with a recess for accommodation of a condensate absorbent, and the body of the cup with a shoulder to serve as a seat for the bottom of the lid. The lid and body are threaded for engagement. By placing a culture medium in the depression, a biological specimen such as urine or blood can be added in just sufficient quantity to wet the culture so pouring and handling are reduced. Culture and analysis can then be undertaken in the usual manner using the cup body as the carrier of the culture medium.

8 Claims, 5 Drawing Figures

CULTURE CUP AND METHOD FOR SAMPLING AND MICROBIAL-COUNT DETERMINATION

BACKGROUND OF THE INVENTION

The invention relates to a culture cup for sampling and microbial-count determination.

A number of screening tests are used to diagnose urinary-tract infections. These include serological, microscopic, biochemical, culture and combined methods.

Of all these methods, the culture method has proved to be the most advantageous, and of its different variants the so called agar dip-slide method has found the widest use because of its handling ease and reliability.

In this method, a slide coated with nutrient agar is dipped in the test liquid whose bacterial count is to be determined, for example, urine, and then incubated. (See M.A.-F. Abdou, Münch. med. Wschr. 119 (1977), No. 24, pp. 837–840.)

For the purpose of a urinalysis, it is customary for the patient to collect the urine at home in a container and take it to the place of examination.

It often happens that the container is not sterile, with the result that the tests are positive when they should not be. Also a shift in the microorganism spectrum may occur during transportation through an increase in contaminants and displacement of the original microorganism or distortion of the bacterial sensitivity by the transfer of R factors from the contaminants to the actual disease-agent.

Moreover, to be able to immerse the slide, a relatively large amount of urine is required, which may be a problem in the case of nursing infants, nervous small children and patients with urinary difficulties.

Finally, suitable containers often are not available or the container used is not tight.

SUMMARY OF THE INVENTION

The invention thus has as its object the provision of a container whereby a microbial count may be made on the principle of wetting the surface of a culture medium with the liquid to be analyzed but which overcomes the above-mentioned drawbacks of transportation and immersion hitherto encountered.

This object is overcome by means of a novel culture cup which includes a cup body and a tightly closing removable cup lid, the bottom of the cup body being provided with depressions for accommodation of at least one culture medium.

The culture cup is given to the patient, his parents or the doctor's assistant in closed, sterile condition. In this way, the quota of falsely positive test results is greatly reduced by comparison with the so-called "fruit-jar method". Patients who are not in need of therapy are spared an unnecessary antibiotic treatment.

Since the culture medium contained in the bottom of the cup need only be wetted, very small amounts of urine will suffice, and the culture cup therefore is particularly well suited for the taking of samples from nursing infants, nervous small children and patients with urinary difficulties.

Since the small amount of urine needed diffuses into the culture medium, the supernatant being discarded prior to transportation, any shaking in the course of transportation will not result in a shifting of the bacterial spectrum or of the bacterial sensitivity.

Moreover, the cup means less work for the personnel of clinics, doctors offices or laboratories since a number of operations can be dispensed with, such as opening the urine container, pouring the urine into a cup, immersing the slide in the urine, letting the slide drain, putting the slide back into its receptacle, and screwing the latter shut. Besides, each of these manipulations poses the hazard that foreign germs might be introduced, and this possibility is virtually eliminated by the new culture cup. The culture cup offers certain advantages also from the standpoint of cost and antipollution since sampling and culture screening with but one device result in material and labor savings and only one cup has to be disposed of instead of separate specimen and bacterial-culture containers.

Finally, the new culture cup may gain wide acceptance because of its handling ease, reliability and low price, and in this way it may bring about a readier acceptance of routine checkups for babies, small children, children of school age, pregnant women and diabetics. Surveys have shown that about 1 to 2% of all children of preschool age, about 5% of all girls and 0.5% of all boys between the ages of 6 and 19, about 5 to 15% of all pregnant women and about 10 to 20% of all diabetics suffer from bacteriuria, which is often nonapparent and which in the absence of treatment may lead to chronic active pyelonephritis with attendant irreversible damage, and routine checkups would therefore contribute greatly to the preservation of public health.

An advantageous refinement of the culture cup consists in provision of a recessed lid bottom which serves to accommodate a condensate absorbent taking up any condensate liquid formed in the closed up.

A further advantageous refinement consists in the bottom of the cup being provided with partitions for creation of a plurality of separate culture-medium compartments permitting not only a microbial total count to be made but also other characteristics of the microorganisms to be determined.

In case of using elective and/or selective culture media, it is possible to identify the microorganisms in the specimen tested.

BRIEF DESCRIPTION OF THE DRAWINGS

The invention will now be explained in greater detail with reference to the accompanying diagrammatic drawings, wherein.

DETAILED DESCRIPTION OF THE INVENTION

Figure 1:
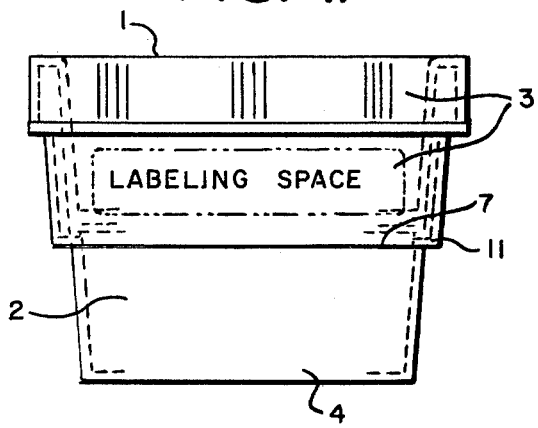
FIG. 1 is a front elevation of the cup in its entirety.

Shown in FIG. 1 is the culture cup 1 as a whole, consisting of a body 2 with a bottom 4 as well as a shoulder 11, a lid 3 with a preferably recessed bottom 7 and, optionally, a space for labeling.

Figure 2:
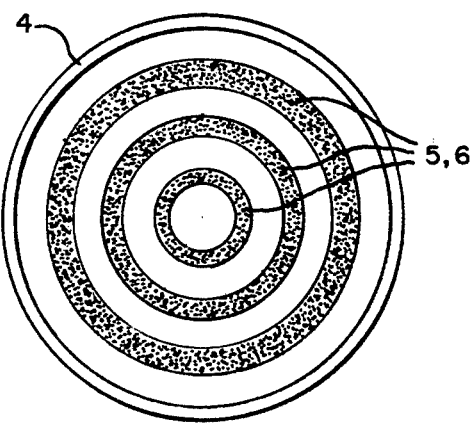
FIG. 2 is a top plan view of the bottom of the cup.

FIG. 2 shows the cup bottom 4 with depressions 5 which are filled with a culture medium 6.

Figure 3:
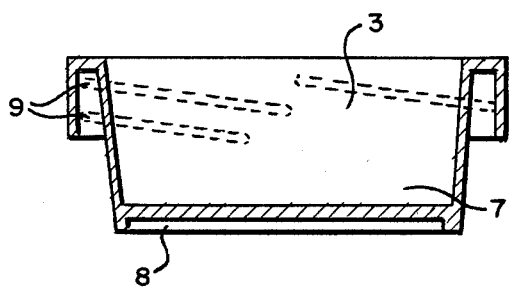
FIG. 3 is a vertical section through the lid of the cup.

Shown in FIG. 3 is the detached cup lid 3 with its preferably recessed bottom 7, a condensate absorbent 8 placed thereon, and a screw thread 9.

Figure 4:
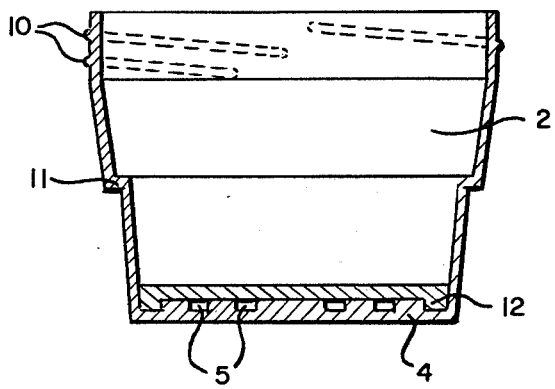
FIG. 4 is a vertical section through the body of the cup.

FIG. 4 shows the separate cup body 2 with depressions 5 in the bottom 4, the shoulder 11 and the screw thread 10, as well as a partition 12 subdividing the bottom.

Figure 5:
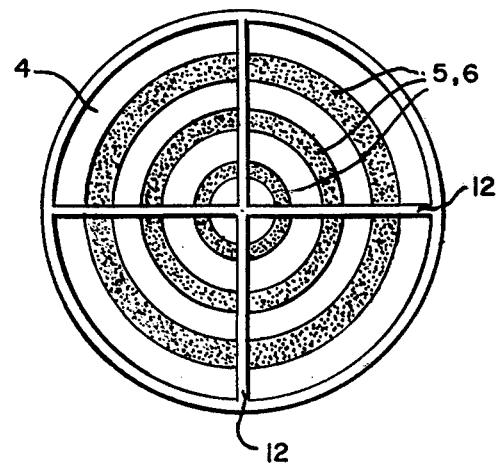
FIG. 5 is a top plan view of the bottom of the cup with partitions.

Shown in FIG. 5, finally, are the cup bottom 4 of FIG. 2 with depressions 5, the culture medium 6, and partitions 12.

The material of construction of the cup is advantageously a cheap, ecologically acceptable disposable material which is not attacked at sterilizing temperatures or with the help of gamma-radiation and lends itself readily to fabrication, as, for example, a plastic which is resistant to temperature changes and gamma-radiation and is minimally pollutive, e.g. polypropylene.

In the drawings, the lid of the cup is shown as a screw cap since this represents the most practical and tight closure. However, any other closure which provides a tight seal and ease of removal of the lid may be used.

The depressions in the bottom of the cup which in the drawings are shown as concentric rings constitute a preferred embodiment as such an arrangement will hold the culture medium particularly well. However, any groove pattern which from a fabricating standpoint is easy to produce may be used.

Cups having the following dimensions have been found to be particularly useful: Overall height of cup with lid in place, about 42 to 44 mm; height of cup body, about 39 to 41 mm; height of lid with recessed bottom, about 23 to 25 mm; height of cup from bottom to shoulder, about 18 to 21 mm; diameter of cup bottom, about 50 to 54 mm; diameter of cup body at top, about 62 to 66 mm; diameter of lid at top, about 68 to 72 mm; slope of cup, about 5°; depth of depressions in bottom of cup, about 1.5 to 3 mm; and height of partitions, if any, about 4 to 6 mm.

When necessary or indicated, larger or smaller cups may be used, of course.

The condensate absorbent may consist of filter paper or of a foamed plastic, for example.

Any of the culture media known in the art for microbial count determinations, particularly in urine, may be used. Examples of such culture media are:

(1) C.L.E.D. agar, described in Kunin, C. M.: Detection, Prevention and Management of Urinary Tract Infections, 2nd ed., Lea & Febiger, Philadelphia, 1974, page 96.

(2) MacConkey's agar, described in Manual of Clinical Microbiology, 2nd ed., Lennette, E. H., Spaulding, E. H., and Traunt, J. P. (editors), American Society for Microbiology, Washington, D.C., 1974, page 908.

The novel culture cup will prove particularly useful when provided with a culture medium incorporating antichemo-therapeutic agents. In addition to the reduction in falsely positive results referred to above, it will then permit a reduction of falsely negative results as well.

While the novel culture cup has been described in conjunction with the sampling and microbial-count determination of urine, it may, of course, be used also in the sampling and microbial-count determination of other test substances.

For example, it is suited for use in the microbial-count determination of lemonades, fruit juices and milk beverages as well as of mineral, spring and well water. It may further be used with cooling cutting liquids, swimming-pool water, sea water and aquariums.

It will be appreciated that the instant specification and claims are set forth by way of illustration and not limitation and that various changes and modifications may be made without departing from the spirit and scope of the present invention.

What is claimed is:

1. A culture cup for sampling and microbial-count determination, comprising a body and a tightly closing removable lid, the lid being provided on its underside with a recess for accommodation of a condensate absorbent and the body of the cup being provided with an internal annular shoulder which serves as a seat for the recessed bottom of the lid, the bottom of the body being provided with depressions for accommodation of at least one culture medium.

2. A culture cup according to claim 1, wherein the depressions in the bottom of the cup are concentric rings.

3. A culture cup according to claim 1, wherein the lid and the body of the cup are provided with mating screw threads.

4. A culture cup according to claim 1, wherein the bottom of the cup on its top is provided with upstanding partitions.

5. A culture cup according to claim 1, containing a culture medium in the depressions.

6. A method of testing a biological specimen for microbial content, comprising adding said specimen in liquid state to the inside of the body of a cup according to claim 5, discarding the specimen, closing the cup body with the lid, transporting the cup and incubating the cup, removing the lid, and counting the colonies to determine the microbiological quality of the specimen.

7. A culture cup according to claim 1, containing a culture medium in the depressions of the body and a condensate absorbent in the recess of the lid.

8. A culture cup according to claim 7, wherein the depressions in the bottom of the cup are concentric rings, the lid and the body of the cup are provided with mating screw threads, and the bottom of the cup on its top is provided with upstanding partitions.

* * * * *